(12) United States Patent
Elliott

(10) Patent No.: US 7,922,664 B2
(45) Date of Patent: Apr. 12, 2011

(54) METHOD AND SYSTEM FOR IMPROVING PHYSIOLOGIC STATUS AND HEALTH VIA ASSESSMENT OF THE DYNAMIC RESPIRATORY ARTERIAL PRESSURE WAVE USING PLETHYSMOGRAPHIC TECHNIQUE

(75) Inventor: Stephen Bennett Elliott, Allen, TX (US)

(73) Assignee: Coherence LLC, Allen, TX (US)

( * ) Notice: Subject to any disclaimer, the term of this patent is extended or adjusted under 35 U.S.C. 154(b) by 0 days.

(21) Appl. No.: 11/732,819

(22) Filed: Apr. 5, 2007

(65) Prior Publication Data

US 2008/0249422 A1    Oct. 9, 2008

(51) Int. Cl.
*A61B 5/02* (2006.01)
*A61B 5/08* (2006.01)

(52) U.S. Cl. ........ 600/484; 600/483; 600/481; 600/485; 600/500

(58) Field of Classification Search ................. 600/488, 600/481, 490–504, 483–486, 508, 509, 513, 600/529; 607/17–26
See application file for complete search history.

(56) References Cited

U.S. PATENT DOCUMENTS

| | | | | |
|---|---|---|---|---|
| 3,850,169 A * | 11/1974 | Gebben et al. | ............... | 600/500 |
| 4,190,886 A * | 2/1980 | Sherman | ..................... | 600/485 |
| 4,669,485 A * | 6/1987 | Russell | ..................... | 600/492 |
| 4,718,426 A * | 1/1988 | Russell | ..................... | 600/492 |
| 4,718,427 A * | 1/1988 | Russell | ..................... | 600/492 |
| 4,718,428 A * | 1/1988 | Russell | ..................... | 600/492 |
| 4,846,189 A * | 7/1989 | Sun | ..................... | 600/492 |
| 5,111,817 A * | 5/1992 | Clark et al. | ................. | 600/323 |
| 5,140,990 A * | 8/1992 | Jones et al. | ................. | 600/480 |
| 5,269,310 A * | 12/1993 | Jones et al. | ................. | 600/480 |
| 5,623,933 A * | 4/1997 | Amano et al. | ............... | 600/500 |
| 5,755,229 A * | 5/1998 | Amano et al. | ............... | 600/500 |
| 6,319,205 B1 * | 11/2001 | Goor et al. | ................. | 600/485 |
| 6,322,515 B1 * | 11/2001 | Goor et al. | ................. | 600/485 |
| 6,358,201 B1 * | 3/2002 | Childre et al. | ............... | 600/300 |
| 6,506,163 B1 * | 1/2003 | Farrell et al. | ................. | 600/486 |
| 6,616,613 B1 * | 9/2003 | Goodman | ................. | 600/504 |
| 6,702,752 B2 * | 3/2004 | Dekker | ..................... | 600/484 |
| 6,896,661 B2 * | 5/2005 | Dekker | ..................... | 600/529 |
| 6,976,963 B2 * | 12/2005 | Clift | ............................. | 600/484 |
| 7,001,337 B2 * | 2/2006 | Dekker | ..................... | 600/484 |
| 7,117,032 B2 * | 10/2006 | Childre et al. | ............... | 600/545 |
| 7,163,512 B1 * | 1/2007 | Childre et al. | ............... | 600/500 |
| 7,458,937 B2 * | 12/2008 | Elliott | ..................... | 600/485 |
| 7,462,151 B2 * | 12/2008 | Childre et al. | ............... | 600/300 |
| 7,479,114 B2 * | 1/2009 | Hartley et al. | ............... | 600/529 |
| 2003/0163050 A1 * | 8/2003 | Dekker | ..................... | 600/483 |
| 2003/0163054 A1 * | 8/2003 | Dekker | ..................... | 600/502 |
| 2005/0124906 A1 * | 6/2005 | Childre et al. | ............... | 600/529 |
| 2006/0155167 A1 * | 7/2006 | Elliott | ..................... | 600/125 |

* cited by examiner

*Primary Examiner* — Charles A Marmor, II
*Assistant Examiner* — Navin Natnithithadha
(74) *Attorney, Agent, or Firm* — Withrow & Terranova, PLLC

(57) ABSTRACT

The present invention specifies a method and system for assessing the dynamic respiratory arterial pressure wave using plethysmographic sensing techniques. The dynamic respiratory arterial pressure wave is measured and plotted for purposes of diagnosis and or remedial biofeedback.

36 Claims, 5 Drawing Sheets

Figure 1:
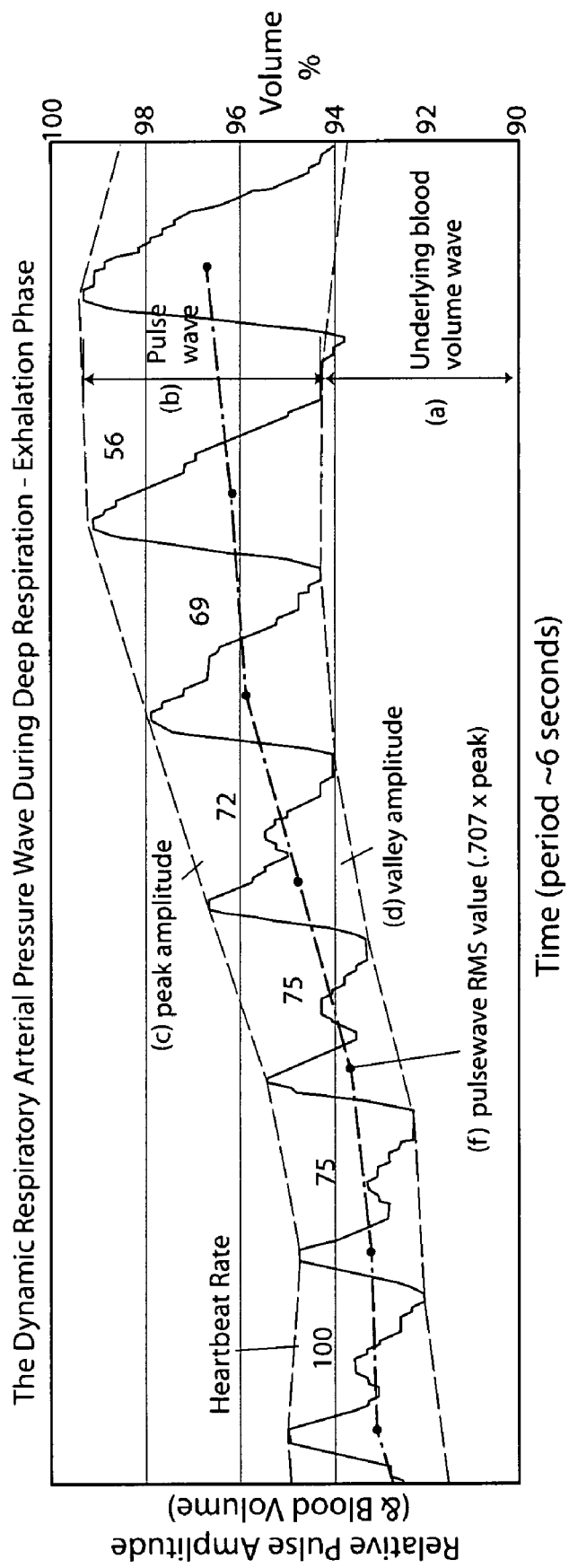

A Theory of Cardiopulmonary Operation at Resonance

Mechanics of Cardiopulmonary Resonance - Schematic View

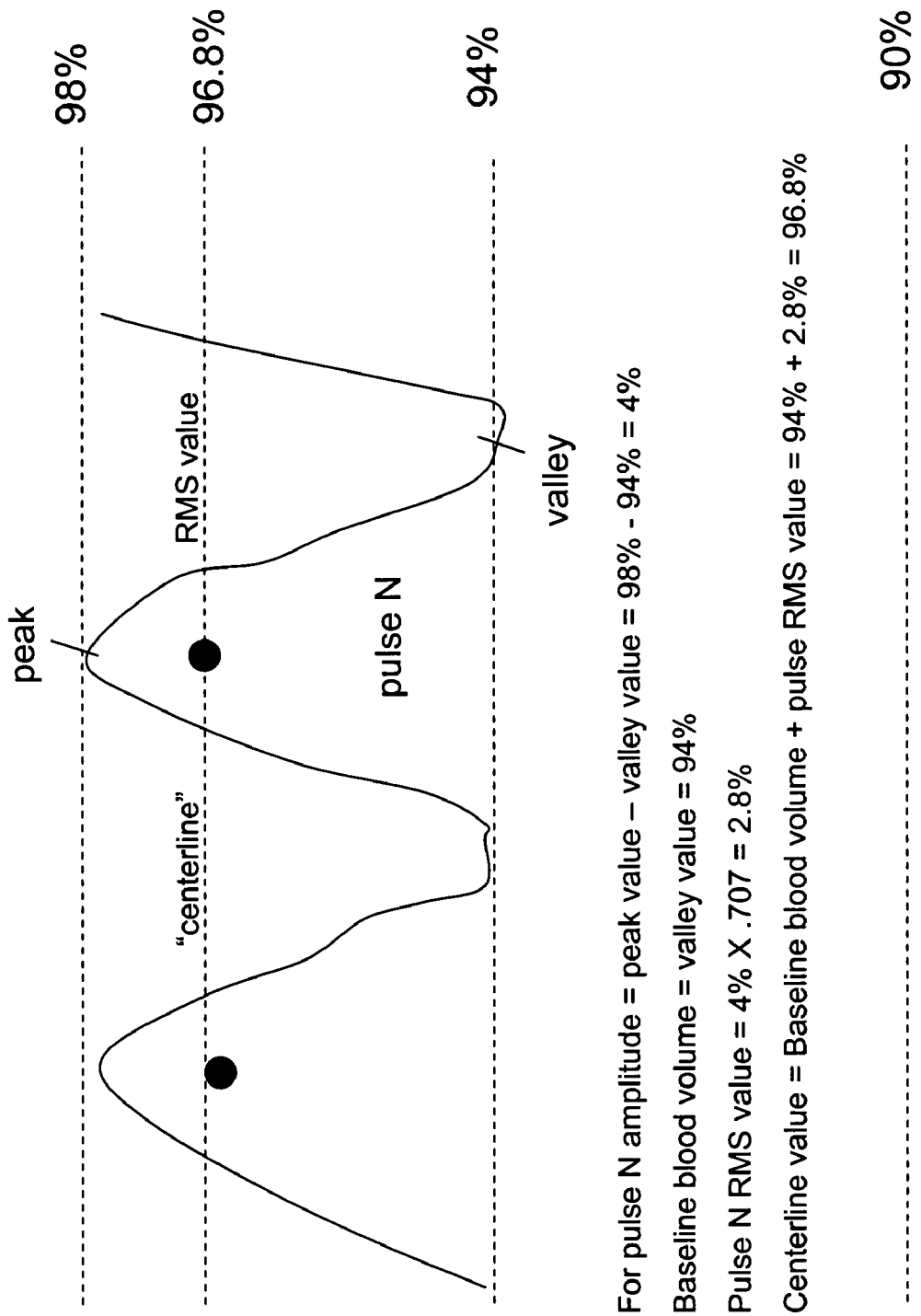

METHOD AND SYSTEM FOR IMPROVING PHYSIOLOGIC STATUS AND HEALTH VIA ASSESSMENT OF THE DYNAMIC RESPIRATORY ARTERIAL PRESSURE WAVE USING PLETHYSMOGRAPHIC TECHNIQUE

RELATED PATENT FILINGS

Method and System for Consciously Synchronizing the Breathing Cycle with the Natural Heart Rate Cycle (Ser. No. 10/699,025), System and Method for Synchronizing the Heart Rate Variability Cycle With The Breathing Cycle (Feb. 19, 2004), Method of Presenting Audible and Visual Cues for Synchronizing the Breathing Cycle With An External Timing Reference for Purposes of Synchronizing The Heart Rate Variability Cycle With The Breathing Cycle (Mar. 15, 2004), Method and System Providing A Fundamental Musical Interval for Heart Rate Variability Synchronization (Mar. 23, 2004), Method and System of Respiratory Therapy Employing Heart Rate Variability Coherence (Ser. No. 10/814,035), Method and System of Breathing Therapy for Reducing Sympathetic Predominance With Consequent Positive Modification of Hypertension (Ser. No. 10/932,636), Method and System for Assessing Breathing Effectiveness Via Assessment of the Dynamic Arterial Pressure Wave Using Oscillometric Measurement Technique (Ser. No. 11/032,662)

FIELD OF THE INVENTION

The present invention relates to the field of human health and in particular to the field of assessing the dynamic respiratory arterial pressure wave and using this information for diagnostic and/or biofeedback purposes for improving health and/or eliciting a desired psycho-physiological change.

The present invention is related to, yet distinctly different from conventional methods of assessing and monitoring arterial pressure.

The present invention is also related to, yet distinctly different from the field of heart rate variability monitoring and biofeedback.

BACKGROUND OF THE INVENTION

Heart rate variability monitoring involves monitoring the heart beat rate and discerning the rate at which the heart beat rate changes. This rate is generally referred to as "heart rate variability" or HRV. The HRV cycle may be used for diagnostic purposes by a health care professional and it may be fed back to the user for purposes of effecting a change in psycho-physiological status. The HRV cycle may be monitored by any means that detects the pulse and measures the inter-beat interval, also know as the "rise-rise" interval. The HRV cycle is typically plotted and displayed graphically for purposes of diagnosis and or biofeedback. A patient or user is typically encouraged to work on modifying amplitude, the average difference between the peak and the valley of the HRV cycle, or the "coherence", i.e. consistency of amplitude, phase, and frequency thereof, for remedial purposes.

It is generally assumed that the heart rate variability phenomenon is a result of autonomic nervous system regulation of blood pressure via the baroreceptor reflex. However, it has not been clear to what the baroreceptor is actually responding.

If this is so, then heart rate variability is a step removed from the actual phenomenon that produces it, i.e. changes in arterial pressure. The more effective and immediate means of moderating physiologic status would be to monitor and feed back the respiratory arterial pressure wave itself. However, until now, it has not been clear why or how the arterial pressure wave is created, or how to monitor it.

To this end, this invention specifies a method for detecting the respiratory arterial pressure wave as a function of blood volume, monitoring the dynamic respiratory arterial pressure wave, measuring its primary physical attributes, and presenting it for diagnostic and or remedial biofeedback purposes.

Under normal quiescent circumstances, arterial pressure is primarily a function of heart beat rate, heart output, and arterial capacity, these factors being regulated by the autonomic nervous system. However, respiration has a very strong effect, dynamic respiratory arterial pressure rising and falling with exhalation and inhalation respectively. This is due to the fact that during deep respiration the lungs and thoracic cavity act as a reservoir for blood, storing it before forwarding it to the left side of the heart and onto the systemic arterial tree.

The pulmonary arterial tree stores 450 ml of blood under normal breathing circumstances, where normal is defined as being relatively fast and shallow, for example 15 breaths per minute with commensurate depth. The pulmonary arterial tree is highly elastic and conforms to changes in thoracic pressure as a function of diaphragmatic action, inhalation or downward movement of the diaphragm resulting in negative thoracic pressure, and exhalation or upward diaphragmatic movement resulting in positive thoracic pressure. The extent of negative and positive pressure depends on the extent of inhalation and exhalation respectively, more complete inhalation and exhalation resulting in stronger negative and positive pressures, respectively. This alternating negative and positive pressure is the reason that air enters the lungs from the external environment coincident with inhalation and exits the lungs coincident with exhalation.

Because of its high elasticity, the pulmonary arterial tree is capable of accommodating up to twice as much blood or ~950 ml during deep inhalation, and evacuating twice a much during deep exhalation. When a person inhales deeply the resulting negative thoracic pressure results in accelerated venous blood flow, filling expanding pulmonary arteries via the right side of the heart. This "storage" reduces blood exiting the lungs toward the left side of the heart, lowering total heart output and systemic arterial pressure. The autonomic nervous system responds to this change by increasing heartbeat rate and constricting (narrowing) arteries, increasing pressure in the arterial tree and thereby limiting the drop due to pulmonary blood storage.

Upon exhalation, the heretofore negative pressure becomes positive, pulmonary arteries contract under positive pressure, forwarding blood through the pulmonary veins to the left side of the heart and into the systemic arterial tree. This results in an increase in systemic arterial pressure. The autonomic nervous system responds to this change by reducing heart beat rate, yet increasing ejection fraction, and relaxing arteries, i.e. enlarging arterial capacity. The net effect is that pressure in the systemic arterial tree increases yet is maintained within viable limits. This results in the respiratory arterial pressure wave that washes through the systemic arterial tree coincident with exhalation.

Baroreceptors are specialized neurons located throughout the arterial system. Their function is that of monitoring arterial pressure. When the baroreceptors sense a decrease in pressure, the autonomic nervous system facilitates an increase. When they sense an increase, the autonomic nervous system facilitates a decrease. In this way, the baroreceptors, in combination with the autonomic nervous system, work in opposition to changes in dynamic respiratory arterial pressure.

The aforementioned relationship between arterial pressure and heart rate is in fact a primary impetus for the heart rate variability phenomenon. Consequently, by monitoring the heart rate variability cycle, at rest, we are able to discern, amongst other things, changes in arterial pressure, rising heart beat rate being indicative of decreasing arterial pressure and falling heart rate being indicative of increasing pressure, heart rate having an inverse relationship with arterial pressure.

This invention proposes the fundamental method of monitoring and utilizing the dynamic respiratory arterial pressure wave itself as the basis for diagnosis and biofeedback for purposes of assessing health condition and or evoking a physiologic change. The advantage of this is that the dynamic respiratory arterial pressure wave is the first order physiological phenomenon. The HRV cycle is second order, i.e. it results from autonomic nervous system regulation of the dynamic arterial pressure wave.

SUMMARY OF THE INVENTION

The invention specifies a system and method employing the plethysmographic detection and monitoring technique. A plethysmograph monitors changes in volume, in this case blood volume as measured in the extremities, for example the forefinger, or the earlobe. Contemporary plethysmographs work on the basis of sensing changes in blood volume via photo detection of blood density. Present day heart rate variability monitors employ plethysmographic detection to sense heartbeat rate, as it is relatively simple, cost effective, and non invasive. Based on the heart beat rate, a plethysmograph detects beat to beat increases in blood volume and density. The monitor calculates the rise-rise interval and divides the interval into 60 seconds, this yielding the "instantaneous" heart beat rate in seconds. But as mentioned, heart rate variability is a second order effect of the dynamic respiratory arterial pressure wave. Consequently, it is far better to monitor the primary physiologic phenomenon—the wave itself.

(Both AC (alternating current) and DC (direct current) optical plethysmographs presently exist, however to the inventor's knowledge they are being used to detect heart beat rate and none are being employed for purposes of assessing the underlying respiratory arterial pressure wave. This is due to the fact there is little to no recognition of the dynamic respiratory arterial pressure wave phenomenon.

Because relatively deep respiration results in large changes in blood flow into and through the systemic arterial tree, blood volume as measured at the extremities changes dramatically. This is to say, when blood flow in the systemic arterial tree increases, blood volume and arterial pressure as measured at the extremities will increase. Likewise, as blood flow in the systemic arterial tree decreases, blood volume and arterial pressure in the extremities will decrease. FIG. 1 demonstrates this effect quite clearly. As such, it is possible to employ the plethysmographic technique to sense these changes in volume directly. Consequently, without concerning ourselves with heart beat rate or heart rate variability, we are able to monitor and or feedback the dynamic respiratory arterial pressure wave itself, a first order determinant of autonomic regulation and the heart rate variability cycle.

Note that it is the object of the invention to assess the magnitude of the blood volume wave, not "arterial pressure". However, it is anticipated that there is correlation between the blood volume wave and conventional arterial pressure.

The invention asserts a method and system for detecting and assessing the dynamic respiratory arterial pressure wave using the plethysmographic technique for purposes of diagnosis and or remedial biofeedback.

BRIEF DESCRIPTION OF THE DRAWING FIGURES

The accompanying drawing figures incorporated in and forming a part of this specification illustrate several aspects of the invention and together with the description serve to explain the principles of the invention.

FIG. 1 presents an increase in blood volume as measured in the index finger over a period of 6 seconds coincident with exhalation, this being the rising aspect of the respiratory arterial pressure wave.

Figure 2:
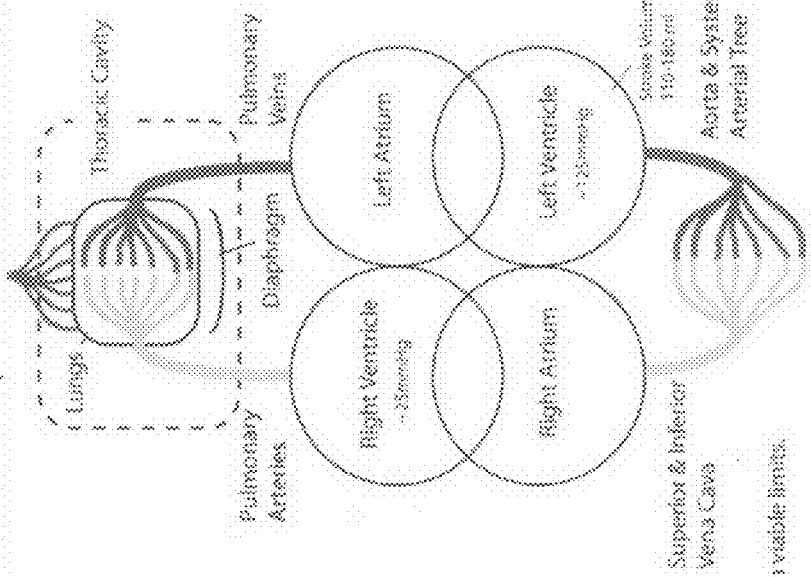

FIG. 2 presents a theory of cardiopulmonary operation at resonance, i.e. optimal frequency and depth of respiration.

Figure 3:
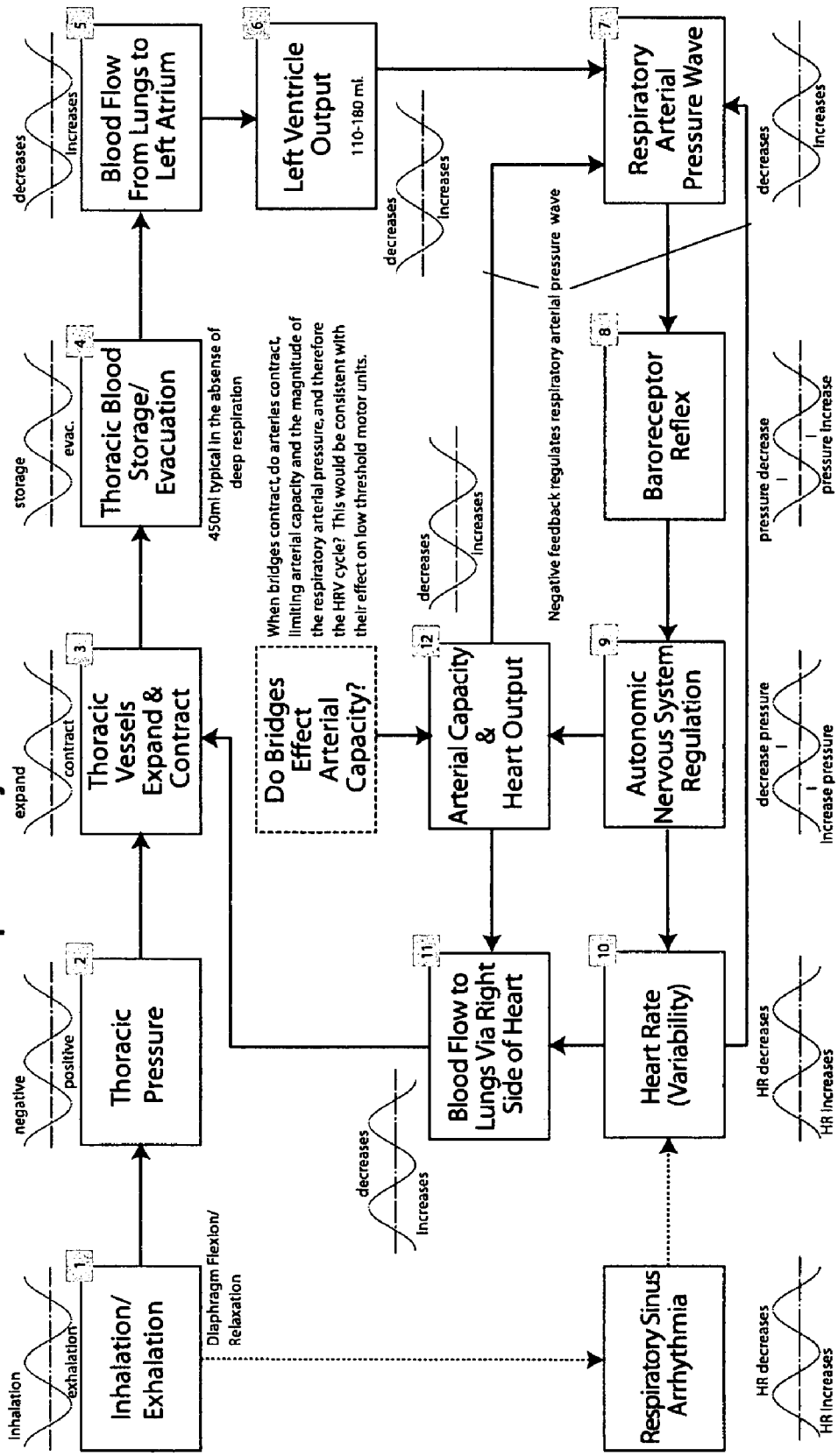

FIG. 3 presents a schematic view of cardiopulmonary operation at resonance.

Figure 4:
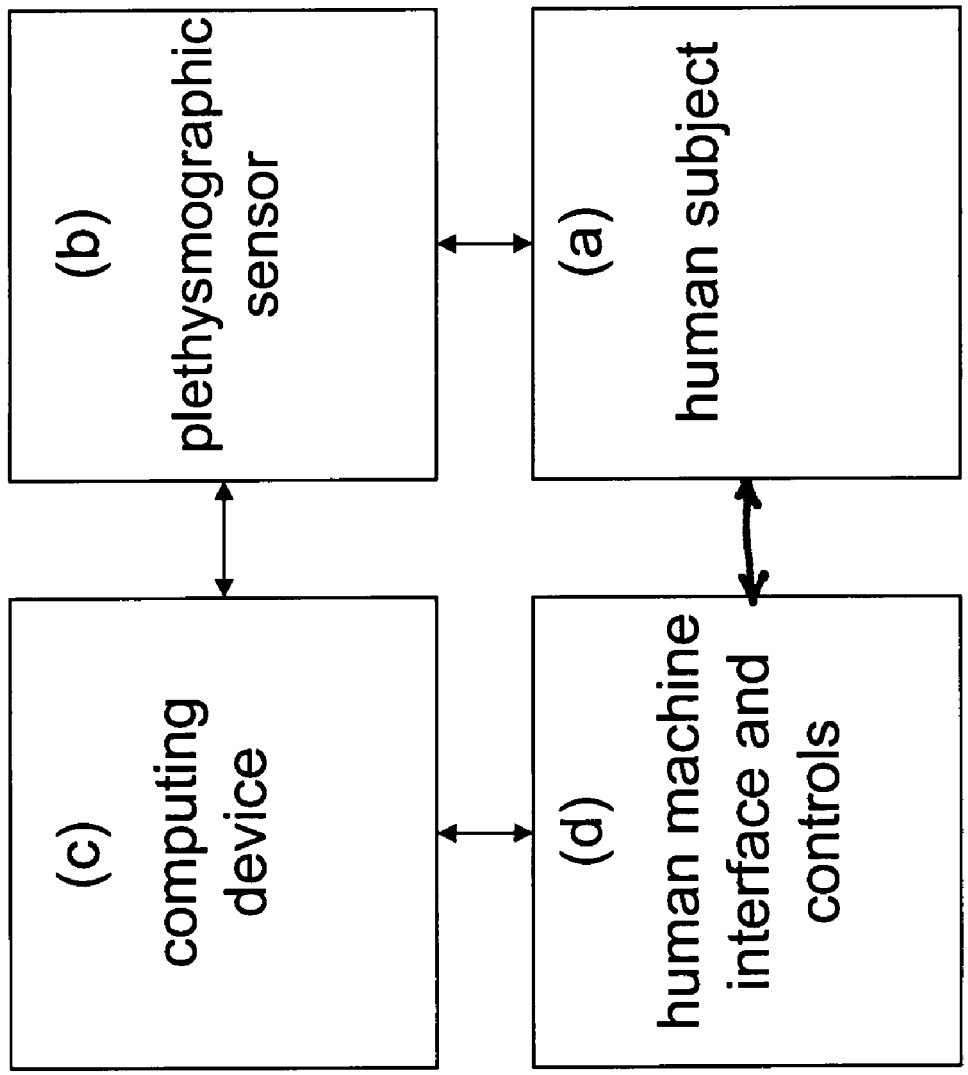

FIG. 4 presents a block diagram of the preferred embodiment of the present invention.

FIG. 5 presents the means by which the dynamic respiratory arterial pressure wave "RMS" value is determined.

DETAILED DESCRIPTION OF THE PREFERRED EMBODIMENTS

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

The present invention advances present state of the art by providing direct monitoring of the dynamic respiratory arterial pressure wave as a function of changes in blood volume as measured via plethysmographic technique including:

a) detecting the presence or absence of an arterial pressure wave, b) if an arterial pressure wave is detected, by assessing magnitude and otherwise characterizing amplitude, rate, and coherence for diagnostic purposes, c) relative to biofeedback, by facilitating the understanding of the relationship between breathing and the respiratory arterial pressure wave, thereby cultivating a dynamic respiratory arterial pressure wave with desirable healthful characteristics.

FIG. 1, presents a view of the respiratory arterial pressure wave during deep respiration, specifically the exhalation phase of the breathing cycle. The X-axis is time, in this case approximately 6 seconds, and the Y-axis is percent of maximum volume. The respiratory arterial pressure wave consists of two major aspects, the underlying blood volume wave (a), and the pulse wave (b). In this case, the blood volume wave is changing between approximately 92 and 94%. The pulse wave rides atop the blood volume wave. In this view, the pulse wave is changing between 2 and 5%. As can be seen the respiratory arterial pressure wave rises with exhalation. While a like view of inhalation is not shown, the wave falls with inhalation, this cycle continuing for as long as respiration is relatively deep and rhythmic. The pulse is superimposed on the blood volume wave, overall volume increasing coincident with evacuation of the pulmonary tree, increased blood flow through the left side of the heart, increasing heart ejection fraction, and relaxing arteries, i.e. expanding arterial capacity and blood flow. As can be seen, amplitude of the pulse wave rises and falls coincident with coincident with underlying blood volume.

There are several measurable components of the wave:
a) the underlying blood volume amplitude correlating with the amplitude of pulse wave valleys
b) pulse wave amplitude
b) pulse wave peak amplitude, correlating with the amplitude of pulse wave peaks
c) pulse wave valley amplitude, correlating with the amplitude of pulse wave valleys Three additional measurements may be derived:
c) the peak to peak amplitude of the pulse wave, the difference between pulse peaks and valleys, and
d) the RMS value of the pulse wave (0.707 times peak)
e) the total amplitude value of the wave which is defined to be the underlying blood volume amplitude plus the RMS value of the pulse wave.

The dynamic respiratory arterial pressure wave has the additional dimensions of frequency, and coherence, i.e. consistency of amplitude, frequency, and phase. Here "frequency" refers to the frequency of the blood volume wave, which includes the pulse but does not concern itself with the rate of the pulse.

Generally, when breathing frequency and depth are optimal, we would expect the frequency and phase of the respiratory arterial pressure wave to follow the frequency and phase of the breathing cycle, total wave amplitude rising with exhalation and falling with inhalation.

More detailed insight into cardiopulmonary operation during respiration may be gained by reviewing FIGS. 2 and 3.

The object of the present invention is the detection and presentation of this dynamic respiratory arterial pressure wave in terms of blood volume over the duration of seconds, minutes, or hours, for diagnostic and remedial purposes. Note that "pressure" is not being measured. However, this application asserts that there is a significant correlation between the amplitude of the respiratory arterial pressure wave and systolic and diastolic arterial pressures. With the aid of FIGS. 2, 3, and 4, the salient aspects of the present method will now be discussed. The high level system involves these elements:
1) A direct current (DC) coupled optical, plethysmograph (b) for sensing changes in blood volume.
2) The plethysmographic sensor is attached to human subject (a).
3) A computing device (c), for the purpose of detecting and processing the output of the plethysmographic sensor, recording the measurement session, and for facilitating programmability aspects including setting of targets and thresholds. The following parameters are measured and optionally presented to the diagnostician or user:
  a. A view of the raw plethysmographic signal is plotted with metrics in near real time
  b. Total amplitude which is equivalent to pulse wave peaks is measured and plotted.
  c. Pulse wave RMS value+the value of the underlying blood volume wave), varying amplitude is plotted and measured in near real time.
  d. Underlying blood volume wave amplitude equivalent to pulse wave valleys is measured and plotted.
  e. Pulse wave amplitude which is the value of the pulse wave peak minus the pulse wave valley.
  f. Frequency of the total wave (pulse wave RMS value plus the value of the underlying blood volume wave). This is a longer term frequency figure and filters out the pulse rate.
  g. Frequency of the pulse rate
  h. Coherence, i.e. amplitude, frequency, and phase consistency of the total wave (pulse wave RMS value+the value of the underlying blood volume wave). This is a longer term coherence figure and filters out the pulse rate.
4) A human machine interface (d) for purposes of presenting the processed output of the plethysmographic sensor to the clinician or user.
5) The system provides for programmably specifying and visually presenting targets and award thresholds in terms of amplitude, frequency, and coherence, i.e. amplitude, frequency, and phase consistency.
6) Amplitude figures are presented as "percent of maximum" where maximum relates to peak blood volume as may occur over a relatively longer duration, for example minutes.
7) The pulse wave RMS value is a filtered (smoothed) measure and is also quantified in terms of peak to peak amplitude in percent, frequency, coherence, i.e. frequency, amplitude, and phase consistency, and serves as the primary metric for diagnosis and or biofeedback. This signal is filtered and smoothed to provide optimal visual comprehension and utility.

FIG. 5 presents the means by which the pulse wave "RMS" value is calculated. It simply involves calculation of the RMS value of the pulse amplitude, then adding this value to the baseline blood volume value. This calculation is performed in near real time for every pulse, smoothed, and plotted accordingly.

Those skilled in the art will recognize improvements and modifications to the preferred embodiments of the present invention. All such improvements and modifications are considered within the scope of the concepts disclosed herein and the claims that follow.

What is claimed is:

1. A method for assessing a dynamic respiratory arterial pressure wave, comprising:
detecting the dynamic respiratory arterial pressure wave as a function of changing blood volume using a plethysmographic device;
assessing at least one characteristic of the dynamic respiratory arterial pressure wave; and
providing at least one output for diagnostic purposes, wherein the at least one output represents the assessed at least one characteristic of the dynamic respiratory arterial pressure wave, whereby providing the at least one output further comprises defining at least one of a visual target and a visual threshold for the dynamic respiratory arterial pressure wave and providing the at least one of the visual target and the visual threshold to at least one of a clinician and a user.

2. The method of claim 1 wherein assessing the at least one characteristic of the dynamic respiratory arterial pressure wave further comprises measuring at least one parameter associated with the dynamic respiratory arterial pressure wave.

3. The method of claim 2 wherein measuring the at least one parameter associated with the dynamic respiratory arterial pressure wave further comprises measuring at least one of amplitude, frequency, phase, coherence, and centerline of the dynamic respiratory arterial pressure wave, wherein measuring the coherence further comprises measuring consistency of the amplitude, the frequency, and the phase of the dynamic respiratory arterial pressure wave.

4. The method of claim 3 wherein providing the at least one output further comprises displaying the at least one of the amplitude, the frequency, the phase, the coherence, and the centerline of the dynamic respiratory arterial pressure wave.

5. The method of claim 3 wherein measuring the amplitude further comprises measuring at least one of a peak amplitude and a valley amplitude of the dynamic respiratory arterial pressure wave.

6. The method of claim 1 wherein assessing the at least one characteristic of the dynamic respiratory arterial pressure wave further comprises calculating a centerline of the dynamic respiratory arterial pressure wave and filtering the centerline, and wherein providing the at least one output further comprises plotting the centerline of the dynamic respiratory arterial pressure wave.

7. The method of claim 6 wherein calculating the centerline of the dynamic respiratory arterial pressure wave further comprises calculating a root mean square (RMS) value of a pulse wave and adding a baseline blood volume value to the RMS value.

8. The method of claim 1 wherein assessing the at least one characteristic of the dynamic respiratory arterial pressure wave further comprises calculating a difference between a peak and a valley of a centerline of the dynamic respiratory arterial pressure wave to determine an amplitude of the dynamic respiratory arterial pressure wave.

9. The method of claim 1 further comprising detecting a peak blood volume and wherein defining the at least one of the target and the threshold for the dynamic respiratory arterial pressure wave further comprises specifying at least one of an amplitude change, a frequency change, and a phase change for the dynamic respiratory arterial pressure wave based upon the peak blood volume.

10. The method of claim 1 further comprising providing at least one of a programmable target and a programmable threshold for the dynamic respiratory arterial pressure wave, and allowing at least one of a clinician and a user to program the at least one of the programmable target and the programmable threshold.

11. The method of claim 1 further comprising identifying a first peak blood volume and wherein assessing the at least one characteristic of the dynamic respiratory arterial pressure wave further comprises characterizing the dynamic respiratory arterial pressure wave relative to the first peak blood volume.

12. The method of claim 11 further comprising identifying a second peak blood volume and wherein assessing the at least one characteristic of the dynamic respiratory arterial pressure wave further comprises determining whether the second peak blood volume is equal to or different from the first peak blood volume.

13. The method of claim 1 wherein assessing the at least one characteristic of the dynamic respiratory arterial pressure wave further comprises calculating an amplitude and a maximum amplitude of the dynamic respiratory arterial pressure wave and providing the at least one output further comprises providing the amplitude as a percentage of the maximum amplitude of the dynamic respiratory arterial pressure wave.

14. The method of claim 1 further comprising instructing at least one of a clinician and a user to modify breathing frequency and depth to affect an increase in amplitude of the dynamic respiratory arterial pressure wave.

15. The method of claim 1 further comprising instructing at least one of a clinician and a user to relax during exhalation to affect an increase in amplitude of the dynamic respiratory arterial pressure wave.

16. The method of claim 1 further comprising using the dynamic respiratory arterial pressure wave to derive a diagnostic indicator of arterial pressure that is not based on measurement of physical arterial pressure, and wherein providing the at least one output further comprises providing the diagnostic indicator.

17. A system for assessing a dynamic respiratory arterial pressure wave, comprising:
a plethysmographic device adapted to sense changing blood volume; and
a computing device adapted to:
detect the dynamic respiratory arterial pressure wave as a function of the changing blood volume;
assess at least one characteristic of the dynamic respiratory arterial pressure wave; and
provide at least one output for diagnostic purposes, wherein the at least one output represents the assessed at least one characteristic of the dynamic respiratory arterial pressure wave, wherein the computing device is further adapted to define at least one of a visual target and a visual threshold for the dynamic respiratory arterial pressure wave and to provide the at least one output based upon the at least one of the visual target and the visual threshold to at least one of a clinician and a user.

18. The system of claim 17 wherein the computing device is further adapted to measure at least one parameter associated with the dynamic respiratory arterial pressure wave.

19. The system of claim 18 wherein the computing device is further adapted to measure at least one of amplitude, frequency, phase, coherence, and centerline of the dynamic respiratory arterial pressure wave.

20. The system of claim 19 wherein in being adapted to measure the coherence, the computing device is further adapted to measure consistency of the amplitude, the frequency, and the phase of the dynamic respiratory arterial pressure wave.

21. The system of claim 20 further comprising a display, and wherein the computing device is further adapted to provide the at least one output based on the at least one of the amplitude, the frequency, the phase, the coherence, and the centerline of the dynamic respiratory arterial pressure wave via the display.

22. The system of claim 19 wherein the computing device is further adapted to measure at least one of a peak amplitude and a valley amplitude of the dynamic respiratory arterial pressure wave.

23. The system of claim 17 further comprising a display, and wherein the computing device is further adapted to calculate a centerline of the dynamic respiratory arterial pressure wave and to provide the at least one output based on the centerline of the dynamic respiratory arterial pressure wave via the display.

24. The system of claim 23 wherein the computing device is further adapted to calculate a root mean square (RMS) value of a pulse wave and to add a baseline blood volume value to the RMS value.

25. The system of claim 17 wherein the computing device is further adapted to calculate a difference between a peak and a valley of a centerline of the dynamic respiratory arterial pressure wave and to determine an amplitude of the dynamic respiratory arterial pressure wave based upon the difference between the peak and the valley of the centerline of the dynamic respiratory arterial pressure wave.

26. The system of claim 17 wherein the computing device is further adapted to detect a peak blood volume and wherein, in being adapted to define the at least one of the target and the threshold for the dynamic respiratory arterial pressure wave, the computing device is further adapted to specify at least one of an amplitude change, a frequency change, and a phase change for the dynamic respiratory arterial pressure wave based upon the peak blood volume.

27. The system of claim 17 wherein the computing device is further adapted to provide at least one of a programmable target and a programmable threshold for the dynamic respiratory arterial pressure wave and to allow at least one of a clinician and a user to program the at least one of the programmable target and the programmable threshold.

28. The system of claim 17 wherein the computing device is further adapted to identify a first peak blood volume and to characterize the dynamic respiratory arterial pressure wave relative to the first peak blood volume, wherein the first peak blood volume is based upon blood volume values sensed via the plethysmographic device.

29. The system of claim 28 wherein the computing device is further adapted to identify a second peak blood volume and to determine whether the second peak blood volume is equal to or different from the first peak blood volume.

30. The system of claim 17 wherein the computing device is further adapted to calculate an amplitude and a maximum amplitude of the dynamic respiratory arterial pressure wave, and to provide the at least one output based upon the amplitude as a percentage of the maximum amplitude of the dynamic respiratory arterial pressure wave.

31. The system of claim 17 wherein the plethysmographic device further comprises a direct current (DC)-coupled plethysmographic device which is further adapted to assess total blood volume including pulse amplitude.

32. The system of claim 17 wherein the computing device is further adapted to instruct at least one of a clinician and a user to modify breathing frequency and depth to affect an increase in amplitude of the dynamic respiratory arterial pressure wave.

33. The system of claim 17 wherein the computing device is further adapted to instruct at least one of a clinician and a user to relax during exhalation to affect an increase in amplitude of the dynamic respiratory arterial pressure wave.

34. The system of claim 17 wherein the computing device is further adapted to use the dynamic respiratory arterial pressure wave to derive a diagnostic indicator of arterial pressure that is not based on measurement of physical arterial pressure and to provide the at least one output based upon the diagnostic indicator.

35. A method for assessing a dynamic respiratory arterial pressure wave comprising an underlying blood volume wave and a pulse wave, comprising:

detecting the dynamic respiratory arterial pressure wave as a function of changing blood volume using a direct current (DC) plethysmographic device; and providing at least one output on a display for diagnostic purposes, wherein the at least one output comprises a complex signal including a DC blood volume wave portion and an alternating current (AC) pulse wave portion, wherein the complex signal is representative of the dynamic respiratory arterial pressure wave as a function of respiration, whereby providing the at least one output further comprises defining at least one of a visual target and a visual threshold for the dynamic respiratory arterial pressure wave and providing the at least one of the visual target and the visual threshold to at least one of a clinician and a user.

36. The method of claim 35, wherein the at least one output further comprises variations in the complex signal as a function of respiration.

\* \* \* \* \*